US006703466B1

(12) United States Patent
Karakelle et al.

(10) Patent No.: US 6,703,466 B1
(45) Date of Patent: Mar. 9, 2004

(54) FOLDABLE INTRAOCULAR LENS OPTICS HAVING A GLASSY SURFACE

(75) Inventors: Mutlu Karakelle, Fort Worth, TX (US); Joseph D. Menczel, Fort Worth, TX (US); Robert A. Scott, Suwanee, GA (US); Charles Freeman, Granbury, TX (US)

(73) Assignee: Alcon, Inc., Hunenberg (CH)

( * ) Notice: Subject to any disclaimer, the term of this patent is extended or adjusted under 35 U.S.C. 154(b) by 8 days.

(21) Appl. No.: 10/171,187

(22) Filed: Jun. 12, 2002

Related U.S. Application Data

(60) Provisional application No. 60/299,010, filed on Jun. 18, 2001.

(51) Int. Cl.[7] .................................................. C08F 32/08
(52) U.S. Cl. ................ 526/259; 526/292.3; 526/292.5; 526/307.5; 526/312; 526/323.1; 623/6.11; 623/6.56; 359/642
(58) Field of Search ............................... 526/292.3, 259, 526/292.5, 307.5, 312, 323.1, 320; 623/6.11, 6.56; 359/642

(56) References Cited

U.S. PATENT DOCUMENTS

| 4,304,895 A | | 12/1981 | Loshaek ...................... 526/313 |
| 4,393,184 A | * | 7/1983 | Tarumi et al. ............... 526/261 |
| 4,515,794 A | | 5/1985 | Emery et al. ................. 514/249 |
| 4,528,311 A | | 7/1985 | Beard et al. ................... 524/91 |
| 4,704,006 A | * | 11/1987 | Sakagami et al. ........ 526/292.3 |
| 4,918,165 A | | 4/1990 | Soll et al. ..................... 530/391 |
| 5,002,571 A | | 3/1991 | O'Donnell, Jr. et al. ......... 623/6 |
| 5,290,892 A | | 3/1994 | Namdaran et al. ........... 526/259 |
| 5,331,073 A | | 7/1994 | Weinschenk, III et al. . 526/264 |
| 5,370,687 A | | 12/1994 | Poler ............................. 623/6 |
| 5,375,611 A | | 12/1994 | Lindquist .................... 128/898 |
| 5,470,932 A | | 11/1995 | Jinkerson .................... 526/312 |
| 5,549,670 A | | 8/1996 | Young et al. ................... 623/6 |
| 5,576,345 A | | 11/1996 | Mansson et al. ............. 514/449 |
| 5,603,774 A | | 2/1997 | LeBoeuf et al. ................ 134/1 |
| 5,693,094 A | | 12/1997 | Young et al. ................... 623/6 |
| 5,693,095 A | * | 12/1997 | Freeman et al. ............ 623/6.56 |
| 5,733,276 A | | 3/1998 | Belkin ............................ 606/6 |
| 5,891,931 A | * | 4/1999 | Leboeuf et al. ................ 522/64 |
| 5,922,821 A | * | 7/1999 | LeBoeuf et al. ............. 526/286 |
| 6,015,842 A | * | 1/2000 | LeBoeuf et al. ............... 522/64 |
| 6,143,027 A | | 11/2000 | Ratner et al. ................... 623/6 |
| 6,187,042 B1 | * | 2/2001 | Sheets et al. ............... 623/6.62 |
| 6,210,438 B1 | * | 4/2001 | Sheets et al. ............... 623/6.56 |
| 6,271,281 B1 | * | 8/2001 | Liao et al. ................... 523/106 |
| 6,353,069 B1 | * | 3/2002 | Freeman et al. ............. 526/319 |
| 6,491,721 B2 | * | 12/2002 | Freeman et al. ........... 623/6.56 |

FOREIGN PATENT DOCUMENTS

| EP | 1 030 194 A1 | | 8/2000 |
| WO | Wo 97/24382 | * | 7/1997 |
| WO | WO 0034804 | * | 6/2000 |

OTHER PUBLICATIONS

Mandle, "Acrylic Lenses Cause Less Posterior Capsule Opacification than PMMA, Silicone IOLs," *Ocular Surgery News*, vol. 14(15), p. 23 (1996).

Nagamoto et al., "Effect of Intraocular Lens Design on Migration of Lens Epithelial Cells Onto the Posterior Capsule," *J. Cataract Refract Surg.*, vol. 23, pp. 866–872 (1997).

Nagata et al., "Optic Sharp Edge or Convexity: Comparison of Effects of Posterior Capsular Opacification," *Jpn J. Ophthal.*, vol. 40, pp. 397–403 (1996).

Oshika et al., "Two Year Clinical Study of a Soft Acrylic Intraocular Lens," *J. Cataract Refract. Surg.*, vol. 22, pp. 104–109 (1996).

Saika et al., "Cell Proliferation on the Outer Anterior Capsule Surface After Extracapsular Lens Extraction in Rabbits," *J. Cataract Refractive Surg.* vol. 23, pp. 1528–1531 (1997).

Ursell et al., "Relationship Between Intraocular Lens Biomaterials and Posterior Capsule Opacification," *J. Cataract Refractive Surg.* vol. 24, pp. 352–360 (1998).

* cited by examiner

*Primary Examiner*—Tatyana Zalukaeva
(74) *Attorney, Agent, or Firm*—Patrick M. Ryan

(57) ABSTRACT

Foldable intraocular lenses having a reduced risk of posterior capsule opacification are disclosed. The foldable intraocular lenses have optics that are prepared such that their surface is glassy and their bulk is rubbery.

10 Claims, No Drawings

FOLDABLE INTRAOCULAR LENS OPTICS HAVING A GLASSY SURFACE

This application claims priority to U.S. Provisional Application, Serial No. 60/299,010, filed Jun. 18, 2001.

FIELD OF THE INVENTION

This invention relates to intraocular lenses. In particular, the present invention relates to foldable intraocular lens optics having a reduced risk of posterior capsule opacification.

BACKGROUND OF THE INVENTION

Foldable intraocular lens ("IOL") materials can generally be divided into three categories: silicone materials, hydrogel materials, and non-hydrogel acrylic materials. Many materials in each category are known. See, for example, Foldable Intraocular Lenses, Ed. Martin et al., Slack Incorporated, Thorofare, N.J. (1993). Biocompatibility varies among different IOL materials within and among each category.

One measure of biocompatability for an IOL can be the incidence of posterior capsule opacification ("PCO"). A number or factors may be involved in causing and/or controlling PCO. For example, the design and edge sharpness of an IOL may be a factor. See, Nagamoto et al., J. Cataract Refract. Surg., 23:866–872 (1997); and Nagata et al., Jpn. J. Ophthalmol., 40:397–403 (1996). See, also, U.S. Pat. Nos. 5,549,670 and 5,693,094. Another factor appears to be the lens material itself. See, for example, Mandle, "Acrylic lenses cause less posterior capsule opacification than PMMA, silicone IOLs," Ocular Surgery News, Vol. 14. No. 15, p.23 (1996). See, also, Oshika, et al., "Two Year Clinical Study of a Soft Acrylic Intraocular Lens," J. Cataract. Refract. Surg., 22:104–109 (1996); and Ursell et al., "Relationship Between Intraocular Lens Biomaterials and Posterior Capsule Opacification," J. Cataract Refract. Surg., 24:352–360 (1998).

One method of addressing the PCO problem involves administering a pharmaceutical agent to the capsular bag area at the time of, or immediately after, extracapsular cataract extraction. See, for example, U.S. Pat. Nos. 5,576,345 (pharmaceutical agent=the cytotoxic agent taxol or an ophthalmically acceptable derivative); 4,515,794; and 5,370,687. Alternatively, the pharmaceutical agent may be tethered to the surface of the IOL material. See, for example, U.S. Pat. No. 4,918,165. The pharmaceutical agents are intended to kill or prevent the growth of proliferating cells that might cause PCO or "secondary cataracts." Yet another method involves the physical destruction or removal of lens epithelial cells. See, Saika et al., J. Cataract Refract. Surg., 23:1528–1531 (1997).

Another method of addressing PCO is the prophylactic laser therapy is method disclosed in U.S. Pat. No. 5,733,276. According to this method, the lens capsule is irradiated with laser irradiation to destroy cells that remain in the lens capsule after extraction of a cataract.

Other methods theorized for reducing the risk of PCO involve adhering the posterior capsule to the IOL at the time of implantation, as in U.S. Pat. No. 5,002,571. According to the '571 patent, a non-biological glue or, preferably, a biological glue, such as fibrin, collagen, or mussel glue, is used to adhere the posterior lens capsule to the posterior surface of an. IOL. The glue may be applied over the entire posterior surface of the IOL or just as an annulus around the outer perimeter of the posterior surface of the IOL.

In contrast, U.S. Pat. No. 5,375,611 discloses a method of reducing the risk of PCO by preventing the adherence of the posterior capsule to the IOL. According to the '611 patent, the posterior surface of the lens capsule itself is chemically modified at the time of extracapsular cataract extraction. The chemical modification is achieved by depositing a water-insoluble stable or permanent layer of a cell attachment-preventing compound onto the posterior surface of the lens capsule. The stable or permanent layer may be a polymer, such as polyethylene glycol, polysaccharides, polyethylenepropylene gylcol, and polyvinyl alcohol derivatives.

What is needed are foldable IOLs having a reduced risk of PCO.

SUMMARY OF THE INVENTION

The present invention provides such foldable IOLs. According to the present invention, foldable IOL optics are prepared so that they have a glassy surface and rubbery bulk state. Specifically, the IOL optics have a $T_g$ (bulk) of about −20 to +25° C., but a $T_g$ (surface) of +30° C. or higher. The IOL optics of the present invention also have an elastic modulus (surface) of about 800 MPa or greater.

Without being bound to any theory, it is believed that IOL optics having mobile surfaces are more susceptible to PCO than those that have less mobile surfaces. IOL optics with rigid surfaces and rubbery cores exhibit improved adhesion to the capsular bag. The rubbery core allows the optic to conform more closely to the shape of the capsule, thus maximizing the contact area between the optic and capsule. At the same time, the rigid optic surface allows sustained or more complete contact with the capsular bag than mobile surfaces.

DETAILED DESCRIPTION OF THE INVENTION

Unless indicated otherwise, all component amounts are presented on a % (w/w) basis.

As used herein, "elastic modulus (surface)" is the elastic modulus determined on the IOL optic surface using an atomic force microscope (using cantilevers having a spring constant of at least 50 N/m, calibrated by the spring against spring method) under normal laboratory (i.e., ambient) conditions. The elastic modulus (surface) value is calculated as the average of elastic modulus (surface) values obtained from at least nine randomly chosen points across the IOL optic surface.

As used herein, "$T_g$ (surface)" is the extrapolated onset of the glass transition of the IOL optic determined using a Micro-Thermal Analyzer 2990 (TA Instruments), calibrated with amorphous polymers at a rate of heating of 10° C./s, under normal laboratory (i.e., ambient) conditions. The $T_g$ (surface) value is calculated as the average of $T_g$ (surface) values obtained from at least nine, preferably at least 18, randomly chosen points across the IOL optic surface.

As used herein, "$T_g$ (bulk)" is the midpoint of the heat capacity increase at the glass transition for a sample of the IOL optic material, measured by differential scanning calorimetry at 10° C./min. under normal laboratory conditions using nitrogen or air as a purge gas.

According to the present invention, IOL optics are prepared so that they have a T. (bulk), which affects the optic's folding and unfolding characteristics, of about −20 to +25° C., but a $T_g$ (surface) of +30° C. or higher. Preferably, the IOL optic has a $T_g$ (bulk) of about −5 to +18° C. and a $T_g$ (surface) of +35° C. or higher. The IOL optics of the present invention also have an elastic modulus (surface) of about 800 MPa or greater, preferably about 1000 MPa or greater.

In addition to the $T_g$ (surface), $T_g$ (bulk) and elastic modulus (surface) properties defined above, the IOL optics of the present invention have an elongation of at least about 150%, preferably at least 200%, and most preferably about 300–600%. This property indicates that the IOL optic generally will not crack, tear or split when folded. Elongation of polymer samples is determined on dumbbell-shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at ambient conditions using an Instron Material Tester (Model No. 4442 or equivalent) with a 50 Newton load cell. The grip distance is set at 14 mm and the crosshead speed is set at 500 mm/minute, and the sample is pulled until failure. The elongation (strain) is reported as the displacement at failure relative to the original grip distance in percentage terms.

The IOL optic has a refractive index of at least about 1.45, and preferably at least about 1.50, as measured by an Abbe' refractometer at 589 nm (Na light source).

The $T_g$ (surface), $T_g$ (bulk), elastic modulus (surface), elongation and refractive index are determined once all processing steps, such as any post-cure polishing or surface treatments (e.g., plasma treatment according to U.S. Pat. No. 5,603,774, the entire contents of which are hereby incorporated by reference) have been conducted and the optic is in a finished form ready for implantation.

IOL optics having the properties described above are capable of being folded or deformed in order to be inserted through small incisions in the eye, such as incisions 4 mm or less, preferably 3 mm or less, in size.

In one embodiment, the IOL optics of the present invention comprise a bulk material and a coating. The bulk material and the coating material independently may be any ophthalmically acceptable IOL material, provided they are selected to provide the $T_g$ (surface), $T_g$ (bulk), elastic modulus (surface), elongation and refractive index properties specified above. Suitable bulk materials include acrylic materials, hydrogel materials and silicone materials. Many ophthalmically acceptable acrylic, hydrogel and silicone materials the are known. Various IOLs made of each of these types of materials are commercially available. Suitable acrylate and methacrylate monomers include alkyl (meth) acrylic monomers, aryl (meth)acrylic monomers, or combinations of both. Such monomers include those disclosed in U.S. Pat. Nos. 5,290,892 and 5,331,073, the entire contents of which are hereby incorporated by reference. Preferred bulk materials include materials comprising a monomer of Formula I below. Most preferred are materials that comprise two monomers of Formula I below wherein one is a methacrylate monomer (A=CH$_3$) and one is an acrylate monomer (A=H).

Suitable coating materials include all ophthalmically acceptable, transparent polymeric materials having a $T_g$ of +30° C. or higher. Examples of such coating materials include, but are not limited to, poly(methylmethacrylate), poly(ethylmethacrylate), poly(propylmethacrylate), poly(t-butyl methacrylate), poly(isobutylmethacrylate), cross-linked polymers of 2-phenylethyl methacrylate, and cross-linked copolymers of 2-phenyethyl acrylate and 2-phenylethyl methacrylate. If desired, the coating material may also contain a cross-linking agent and optionally a UV- and/or blue-light absorbing chromophore. Preferred coating materials include cross-linked polymers of 2-phenylethyl methacrylate, poly(isobutylmethacrylate) and poly(methylmethacrylate).

The coating materials should be applied to form a coating layer approximately 10–500 nm thick, preferably approximately 10–100 nm thick. The coating material can be applied using conventional coating techniques, such as plasma polymerization, graft polymerization, film-forming and solution coating techniques. It may be desirable, depending upon the substrate material, to condition the substrate surface (e.g., by plasma activation) before applying the coating.

In another embodiment, the optics of the present are not formed by applying a coating layer to a substrate, but are instead formed by curing a copolymeric material such that the resulting surface is glassy and the bulk is rubbery. In this embodiment, the optics are made of a copolymer that comprises two lens-forming monomers have different reactivity ratios, where the homopolymer of the monomer having the higher reactivity ratio has a higher glass transition temperature ($T_g$) relative to the homopolymer of the other monomer.

Preferably, the copolymer used to form the IOL optic of the present invention comprises at least one aryl (meth) acrylic monomer of Formula I below. Most preferably, the copolymer consists essentially of two aryl (meth)acrylic monomers of Formula I below and a cross-linking component.

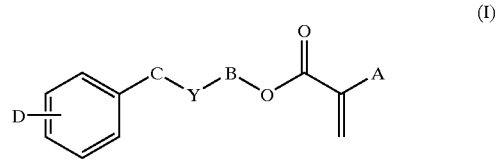
(I)

wherein: A is H, CH$_3$, CH$_2$CH$_3$, or CH$_2$OH;
B is (CH$_2$)m or [O(CH$_2$)$_2$]$_n$;
C is (CH$_2$);
m is 0–6;
n is 0–10;
Y is nothing, O, S, or NR, provided that if Y is O, S, or NR, then B is (CH$_2$)$_m$;
R is H, CH$_3$, C$_n$H$_{2n+1}$ (n=1–10), iso-OC$_3$H$_7$, C$_6$H$_5$, or CH$_2$C$_6$H$_5$;
w is 0–6, provided that m+w≦8; and
D is H, C$_1$–C$_4$ alkyl, C$_1$–C$_4$ alkoxy, C$_6$H$_5$, CH$_2$C$_6$H$_5$ or halogen.

Monomers of Formula I are known and include, but are not limited to: 2-phenoxyethyl acrylate; 2-(phenylthio)ethyl acrylate; 2-(phenylamino)ethyl acrylate; phenyl acrylate; benzyl acrylate; 2-phenylethyl acrylate; 3-phenylpropyl acrylate; 3-phenoxypropyl acrylate; 4-phenylbutyl acrylate; 4-phenoxybutyl acrylate; 4-methylphenyl acrylate; 4-methylbenzyl acrylate; 2-(2-methylphenyl)ethyl acrylate; 2-(3-methylphenyl)ethyl acrylate; 2-(4-methylphenyl)ethyl acrylate; and their corresponding methacrylate compounds.

Preferred aryl (meth)acrylic monomers for use in the materials of the present invention are those wherein A is H or CH$_3$, B is (CH2)m, m is 2–5, Y is nothing or O, w is 0–1, and D is H. Most preferred are 4-phenylbutyl methacrylate; 5-phenylpentyl methacrylate; 2-benzyloxyethyl methacrylate; 3-benzyloxypropyl methacrylate; 2-phenylethyl acrylate; 2-phenoxyethyl acrylate; 3-phenylpropyl acrylate; 3-phenoxypropyl acrylate; 4-phenylbutyl acrylate; 4-phenoxybutyl acrylate; and their corresponding methacrylate compounds.

In the most preferred case where the copolymer consists essentially of two aryl (meth)acrylic monomers of Formula I, the copolymer preferably contains at least one lens-forming monomer of Formula I that is a methacrylate monomer (A=CH$_3$) and at least one lens-forming monomer of Formula I that is an acrylate monomer (A=H).

Depending on the target T$_g$ (bulk), T$_g$ (surface), elastic modulus (surface) and elongation properties and the difference in reactivity ratios between the two lens-forming monomers, the relative amounts of each-lens-forming monomer and cross-linking monomer can be adjusted. As one skilled in the art appreciates, the greater the difference in reactivity ratios between the two lens-forming monomers and the higher the homopolymer T$_g$ of the monomer having the higher reactivity ratio, the less of the higher reactivity ratio monomer that is needed to obtain the same target effect. Preferably, the higher reactivity ratio monomer is present in an amount that is less than that of the lower reactivity ratio monomer. A preferred ingredient concentration range is approximately 40–90% for the lower reactivity ratio lens forming monomer and approximately 45–10% for the higher reactivity ratio lens forming monomer.

The copolymers used to form the optics of the present invention are cross-linked. The copolymerizable cross-linking agent used in the copolymers of this invention may be any terminally ethylenically unsaturated compound having more than one unsaturated group. Combinations of cross-linking monomers are also suitable. Suitable cross-linking agents for meth(acrylic) lens-forming monomers include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, 1,4-butanediol diacrylate and the like. Generally, the amount of the cross-linking component ranges from about 0.1–15%.

In either embodiment described above, the optic compositions optionally include one or more ingredients selected from the group consisting of UV absorbers, blue-light blocking colorants, and fluorinated monomers.

Ultraviolet absorbing chromophores can be any compound which absorbs light having a wavelength shorter than about 400 nm, but does not absorb any substantial amount of visible light. It is preferred to use an ultraviolet absorbing compound that is copolymerizable with the monomers chosen for use in the IOL optic copolymer. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 49528,311.

If a blue-light absorbing compound, e.g. a yellow dye, is included in the optic copolymeric materials, it is preferably copolymerizable with the monomers chosen for use in the IOL optic copolymer. Suitable polymerizable blue-light blocking chromophores include those disclosed in U.S. Pat. No. 5,470,932.

The materials used to form the optics of the present invention are cured using conventional thermal and/or light-activated curing processes. Preferred thermal initiators include peroxy free-radical initiators, such as t-butyl (peroxy-2-ethyl)hexanoate and di-(tert-butylcyclohexyl) peroxydicarbonate (commercially available as Perkadoxe 16 from Akzo Chemicals Inc., Chicago, Ill.). Particularly in cases where the lens material does not contain a blue-light absorbing chromophore, preferred photoinitiators include benzoylphosphine oxide photoinitiators, such as the blue-light initiator 2,4,6-trimethyl-benzoyldiphenylphosphine oxide, commercially available as Lucirin® TPO from BASF Corporation (Charlotte, N.C.).

The curing parameters, e.g., length of exposure and temperature or intensity of light source, are preferably chosen to accomplish complete polymerization. In the second embodiment above, however, the curing conditions are controlled so that the required T$_g$ (bulk), T$_g$ (surface) and elastic modulus (surface) properties are achieved. For example, thermal initiators are used with a curing temperature/time schedule designed to cure the copolymeric material relatively slowly. As a result of the reactivity ratio difference between the two lens-forming co-monomers and as a result of the co-monomers being chosen so that a homopolymer of the monomer having the higher (faster) reactivity ratio has a T$_g$ higher than a homopolymer of the other, the outer portion of the cured optic material is rich in the higher reactivity ratio monomer and has a T$_g$ which is higher than that of the bulk material. If the material is cured too fast or the reactivity rates or T$_g$'s of the chosen lens-forming monomers are too close to each other, the required difference between the T$_g$ (surface) and T$_g$ (bulk) may not be achieved.

Once the optic has been prepared, it may be processed as desired or required, including, for example, tumble-polishing and plasma treatment, such as disclosed in U.S. Pat. No. 5,603,774. The required T$_g$ (surface), T$_g$ (bulk) and elastic modulus (surface) properties are determined with the optic in the dry state after all post-cure processing is completed and the optic is ready for implantation.

The IOL optic of the present invention may be of any suitable shape and size. The IOL optic may be attached to one or more haptics of the same or different material to form what are known as one- or multi-piece IOLs. The optic preferably does not contain a tumble-polished edge, as some reports associate square edges with reduced PCO problems. See, for example, Nagamoto et al., J. Cataract Refract. Surg., 23:866–872 (1997); and Nagata et al., Jpn. J. Ophthalmol., 40:397–403 (1996).

The invention will be further illustrated by the following examples, which are intended to be illustrative, but not limiting.

COMPARATIVE EXAMPLE 1

Two model #MA30BA, 21.5 D ACRYSOF® IOLs (Alcon Laboratories, Inc., Ft. Worth, Tex.) were analyzed to determine the T$_g$ (surface), T$_g$ (bulk) and elastic modulus (surface) and the following results were obtained:

First sample: T$_g$ (surface)=26.6±2.1° C.
T$_g$ (bulk)=11.0° C.
elastic modulus (surface)=681±165 MPa Second sample: T$_g$ (surface)=25.9±2.3° C.
T$_g$ (bulk)=11.5° C.
elastic modulus (surface)=453±22 MPa

COMPARATIVE EXAMPLE 2

Two model # MA30BA IOLs were analyzed to determine their T$_g$ (surface) and T$_g$ (bulk) values. In both cases, the T$_g$ (bulk) was 11.0° C. In the case of the first sample, 18 measurements were taken and averaged to give an average T$_g$ (surface) of 27° C. In the case of second sample, 17 measurements were taken and averaged to give an average T$_g$ (surface) of 26° C.

EXAMPLES 1–2

IOL optic materials were prepared by thermally curing a formulation comprising 65 wt % phenylethyl acrylate, 30 wt % phenylethyl methacrylate, 3.2 wt % 1,4-butanediol diacrylate, and 1.8 wt % o-methallyl Tinuvin P, with 1 wt % Perkadox-16 initiator. Each IOL optic thus prepared was treated in one of three ways: no further treatment (Comparative Example 3); immersion for 5 seconds in a 5% (w/v) solution of poly(methyl methacrylate) (PMMA) in 2.5:1 acetone:methylene chloride, followed by drying at 50° C. for a period of two hours (Example 1); or immersion for 5 seconds in a 5% (w/v) solution of poly(isobutyl methacrylate) (PIMA) in acetone, followed by drying at 50° C. for a period of two hours (Example 2).

Three samples of each type were analyzed to determine the $T_g$ (surface), $T_g$ (bulk), and elastic modulus. The results are shown in Table 1 below. Values in the table reflect averages over multiple sampling points for each tested sample.

TABLE 1

| Sample | $T_g$ (surface) °C. | $T_g$ (bulk) °C. | Elastic Modulus (surface) MPa |
|---|---|---|---|
| Comp. Ex. 3 | 19 ± 1 | 11.0 ± 0 | 110 ± 20 |
| Example 1 | 95 ± 4 | 10.5 ± 0.5 | 1905 ± 738 |
| Example 2 | 85 ± 2 | 10.5 ± 1.5 | 903 ± 122 |

EXAMPLE 3

A copolymer was formed by mixing 72% 2-phenylethyl acrylate, 23% methyl methacrylate, 3.6% 1,4-butanediol diacrylate, and 1.4% o-methallyl Tinuvin P, with 1.8% Perkadox-16s added to the mixture as a thermal initiator. The copolymer was cured in a polypropylene mold in the shape of an IOL optic using the following curing profile: seven hours at 70° C., followed by seven hours at 100° C. After curing, the optic was analyzed to determine the $T_g$ (surface), $T_g$ (bulk) and elastic modulus (surface) properties and the following results were obtained:

$T_g$ (surface)=28.0±5.0° C.

$T_g$ (bulk)=13.5° C.

elastic modulus (surface)=946±165 Mpa

Although this example is not characterized as a comparative example, it does not meet the stated $T_g$ (surface) value of +30° C. or higher. The measured $T_g$ (surface) was very close, however, and it is believed that the ratio of the 2-phenylethyl acrylate and methyl methacrylate monomers and/or the curing profile can be readily adjusted in order to obtain an optic that does meet the stated $T_g$ (surface), $T_g$ (bulk), and elastic modulus (surface) properties.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A foldable intraocular lens optic having a glassy surface but rubbery bulk and a reduced risk of posterior capsule opacification wherein the optic has a refractive index of at least about 1.45, an elongation of at least about 150%, a $T_g$ (bulk) of about −20 to +25° C., a $T_g$ (surface) of +30° C. or higher and an elastic modulus (surface) of about 800 MPa or greater.

2. The optic of claim 1 wherein the optic has a $T_g$ (bulk) of about −5 to +18° C.

3. The optic of claim 1 wherein the optic has a $T_g$ (surface) of +35° C. or higher.

4. The optic of claim 1 wherein the optic has an elastic modulus (surface) of about 1000 MPa or greater.

5. The optic of claim 1 wherein the optic has an elongation of about 300–600%.

6. The optic of claim 1 wherein the optic has a refractive index of at least about 1.50.

7. The optic of claim 1 wherein the optic comprises at least one aryl (meth)acrylic monomer of the formula

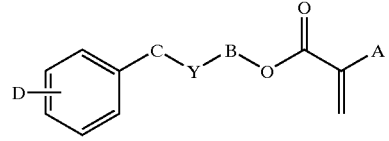

(I)

wherein: A is H, $CH_3$, $CH_2CH_3$, or $CH_2OH$;

B is $(CH_2)_m$ or $[O(CH_2)_2]_n$;

C is $(CH_2)_w$;

m is 0–6;

n is 0–10;

Y is nothing, O, S, or NR, provided that if Y is O, S, or NR, then B is $(CH_2)_m$;

R is H, $CH_3$, $C_nH_{2n+1}$ (n=1–10), iso-$OC_3H_7$, $C_6H_5$, or $CH_2C_6H_5$;

w is 0–6, provided that m+w≦8; and

D is H, $C_1$–$C_4$ alkyl, $C_1$–$C_4$ alkoxy, $C_6H_5$, $CH_2C_6H_5$ or halogen.

8. The optic of claim 7 wherein A is H or $CH_3$, B is $(CH_2)_m$, m is 2–5, Y is nothing or O, w is 0–1, and D is H.

9. The optic of claim 1 wherein the optic comprises a bulk material and a coating layer, wherein the coating layer is approximately 10–500 nm thick.

10. The optic of claim 1 wherein the optic comprises a copolymer comprising two lens-forming monomers have different reactivity ratios, where the homopolymer of the monomer having the higher reactivity ratio has a higher glass transition temperature ($T_g$) relative to the homopolymer of the other monomer.

* * * * *